(12) United States Patent
Weinstein et al.

(10) Patent No.: US 9,265,438 B2
(45) Date of Patent: Feb. 23, 2016

(54) LOCATING FEATURES IN THE HEART USING RADIO FREQUENCY IMAGING

(75) Inventors: Uriel Weinstein, Maskeret Batya (IL); Assaf Bernstein, Givat Nilly (IL); Eyal Cohen, Ariel (IL); Vered Cohen Sharvit, Modiin (IL)

(73) Assignee: Kyma Medical Technologies Ltd., Tel Aviv (IL)

( * ) Notice: Subject to any disclaimer, the term of this patent is extended or adjusted under 35 U.S.C. 154(b) by 630 days.

(21) Appl. No.: 13/513,396

(22) PCT Filed: Dec. 1, 2009

(86) PCT No.: PCT/IB2009/055438
§ 371 (c)(1),
(2), (4) Date: Sep. 12, 2012

(87) PCT Pub. No.: WO2011/067623
PCT Pub. Date: Jun. 9, 2011

(65) Prior Publication Data
US 2012/0330151 A1    Dec. 27, 2012

(51) Int. Cl.
*A61B 5/05* (2006.01)
*A61B 5/11* (2006.01)
*A61B 8/00* (2006.01)
*A61B 5/08* (2006.01)
*A61B 8/08* (2006.01)
*A61B 5/0402* (2006.01)
(Continued)

(52) U.S. Cl.
CPC ............ *A61B 5/0507* (2013.01); *A61B 5/05* (2013.01); *A61B 5/08* (2013.01); *A61B 5/1107* (2013.01); *A61B 5/4878* (2013.01); *A61B 8/085* (2013.01); *A61B 8/4254* (2013.01); *A61B 5/0402* (2013.01); *A61B 5/6823* (2013.01); *A61B 5/7285* (2013.01); *A61B 2560/0412* (2013.01); *A61B 2562/0209* (2013.01); *A61B 2562/14* (2013.01); *A61B 2562/166* (2013.01); *A61N 1/36578* (2013.01)

(58) Field of Classification Search
CPC ......................................................... A61B 5/05
USPC .......................... 600/407, 425, 427, 437, 439
See application file for complete search history.

(56) References Cited

U.S. PATENT DOCUMENTS

| | | |
|---|---|---|
| 4,240,445 A | 12/1980 | Durney et al. |
| 4,344,440 A | 8/1982 | Aaby et al. |
| 4,557,272 A | 12/1985 | Carr |

(Continued)

FOREIGN PATENT DOCUMENTS

| | | |
|---|---|---|
| EP | 1834588 A1 | 9/2007 |
| JP | 2007-061359 A | 3/2007 |

(Continued)

OTHER PUBLICATIONS

International Search Report for International Application No. PCT/IB2009/055438, date of mailing: Jul. 20, 2010.

(Continued)

*Primary Examiner* — Peter Luong
(74) *Attorney, Agent, or Firm* — Cooley LLP

(57) ABSTRACT

Diagnostic apparatus (20) includes an antenna 32, which is configured to direct radio frequency (RF) electromagnetic waves into a living body and to generate signals responsively to the waves that are scattered from within the body. Processing circuitry (36) is configured to process the signals so as to locate a feature in a blood vessel in the body.

19 Claims, 7 Drawing Sheets

(51) Int. Cl.
    *A61B 5/00*     (2006.01)
    *A61N 1/365*    (2006.01)

(56) References Cited

U.S. PATENT DOCUMENTS

| | | |
|---|---|---|
| 4,632,128 A | 12/1986 | Paglione et al. |
| 4,640,280 A | 2/1987 | Sterzer |
| 4,641,659 A | 2/1987 | Sepponen |
| 4,774,961 A | 10/1988 | Carr |
| 4,825,880 A | 5/1989 | Stauffer et al. |
| 4,926,868 A | 5/1990 | Larsen |
| 4,958,638 A | 9/1990 | Sharpe |
| 4,986,870 A | 1/1991 | Frohlich |
| 5,003,622 A | 3/1991 | Ma et al. |
| 5,109,855 A | 5/1992 | Gunter |
| 5,394,882 A | 3/1995 | Mawhinney |
| 5,404,877 A | 4/1995 | Nolan |
| 5,540,727 A | 7/1996 | Tockman et al. |
| 5,549,650 A | 8/1996 | Bornzin et al. |
| 5,668,555 A | 9/1997 | Starr |
| 5,704,355 A | 1/1998 | Bridges |
| 5,766,208 A | 6/1998 | McEwan |
| 5,807,257 A | 9/1998 | Bridges |
| 5,829,437 A | 11/1998 | Bridges |
| 5,865,177 A * | 2/1999 | Segawa .......... 600/410 |
| 5,967,986 A | 10/1999 | Cimochowski et al. |
| 6,019,724 A | 2/2000 | Gronningsaeter et al. |
| 6,061,589 A | 5/2000 | Bridges et al. |
| 6,064,903 A | 5/2000 | Riechers et al. |
| 6,093,141 A | 7/2000 | Mosseri et al. |
| 6,144,344 A | 11/2000 | Kim |
| 6,193,669 B1 | 2/2001 | Degany et al. |
| 6,233,479 B1 | 5/2001 | Haddad et al. |
| 6,330,479 B1 | 12/2001 | Stauffer |
| 6,454,711 B1 | 9/2002 | Haddad et al. |
| 6,480,733 B1 | 11/2002 | Turcott |
| 6,526,318 B1 | 2/2003 | Ansarinia |
| 6,592,518 B2 | 7/2003 | Denker et al. |
| 6,604,404 B2 | 8/2003 | Paltieli et al. |
| 6,729,336 B2 | 5/2004 | Da Silva et al. |
| 6,730,033 B2 | 5/2004 | Yao et al. |
| 6,755,856 B2 | 6/2004 | Fierens et al. |
| 6,940,457 B2 | 9/2005 | Lee et al. |
| 7,020,508 B2 | 3/2006 | Stivoric et al. |
| 7,122,012 B2 | 10/2006 | Bouton et al. |
| 7,130,681 B2 | 10/2006 | Gebhardt et al. |
| 7,191,000 B2 | 3/2007 | Zhu et al. |
| 7,197,356 B2 | 3/2007 | Carr |
| 7,266,407 B2 | 9/2007 | Li et al. |
| 7,267,651 B2 | 9/2007 | Nelson |
| 7,272,431 B2 | 9/2007 | McGrath |
| 7,280,863 B2 | 10/2007 | Shachar |
| 7,454,242 B2 | 11/2008 | Fear et al. |
| 7,474,918 B2 | 1/2009 | Frants et al. |
| 7,479,790 B2 | 1/2009 | Choi |
| 7,493,154 B2 | 2/2009 | Bonner et al. |
| 7,529,398 B2 | 5/2009 | Zwirn et al. |
| 7,570,063 B2 | 8/2009 | Van Veen et al. |
| 7,591,792 B2 | 9/2009 | Bouton |
| 7,697,972 B2 | 4/2010 | Verard et al. |
| 7,719,280 B2 | 5/2010 | Lagae et al. |
| 7,747,302 B2 | 6/2010 | Milledge et al. |
| 7,868,627 B2 | 1/2011 | Turkovskyi |
| 8,295,920 B2 | 10/2012 | Bouton et al. |
| 8,352,015 B2 | 1/2013 | Bernstein et al. |
| 2002/0032386 A1 | 3/2002 | Sackner et al. |
| 2002/0045836 A1 | 4/2002 | Alkawwas |
| 2002/0049394 A1* | 4/2002 | Roy et al. ............ 600/594 |
| 2002/0050954 A1 | 5/2002 | Jeong-Kun et al. |
| 2002/0147405 A1 | 10/2002 | Denker et al. |
| 2003/0036713 A1 | 2/2003 | Bouton et al. |
| 2003/0088180 A1 | 5/2003 | Van Veen et al. |
| 2003/0100815 A1 | 5/2003 | Da Silva et al. |
| 2003/0219598 A1 | 11/2003 | Sakurai |
| 2004/0015087 A1 | 1/2004 | Boric-Lubecke et al. |
| 2004/0077952 A1 | 4/2004 | Rafter et al. |
| 2004/0249257 A1 | 12/2004 | Tupin et al. |
| 2004/0261721 A1 | 12/2004 | Steger |
| 2005/0038503 A1 | 2/2005 | Greenhalgh et al. |
| 2005/0107693 A1 | 5/2005 | Fear et al. |
| 2005/0245816 A1 | 11/2005 | Candidus et al. |
| 2006/0009813 A1 | 1/2006 | Taylor et al. |
| 2006/0265034 A1 | 11/2006 | Aknine et al. |
| 2007/0016032 A1 | 1/2007 | Aknine |
| 2007/0016050 A1 | 1/2007 | Moehring et al. |
| 2007/0100385 A1 | 5/2007 | Rawat |
| 2007/0123770 A1 | 5/2007 | Bouton et al. |
| 2007/0135721 A1 | 6/2007 | Zdeblick |
| 2007/0152812 A1 | 7/2007 | Wong et al. |
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0030284 A1 | 2/2008 | Tanaka et al. |
| 2008/0036668 A1 | 2/2008 | White et al. |
| 2008/0097199 A1 | 4/2008 | Mullen |
| 2008/0129511 A1 | 6/2008 | Yuen et al. |
| 2008/0167566 A1 | 7/2008 | Unver et al. |
| 2008/0169961 A1 | 7/2008 | Steinway et al. |
| 2008/0183247 A1 | 7/2008 | Harding |
| 2008/0200802 A1 | 8/2008 | Bhavaraju et al. |
| 2008/0224688 A1 | 9/2008 | Rubinsky et al. |
| 2008/0269589 A1 | 10/2008 | Thijs et al. |
| 2008/0283282 A1 | 11/2008 | Kawasaki et al. |
| 2008/0294036 A1 | 11/2008 | Hoi et al. |
| 2008/0316124 A1 | 12/2008 | Hook |
| 2009/0048500 A1 | 2/2009 | Corn |
| 2009/0076350 A1 | 3/2009 | Bly et al. |
| 2009/0153412 A1 | 6/2009 | Chiang et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman |
| 2009/0281412 A1 | 11/2009 | Boyden et al. |
| 2009/0299175 A1 | 12/2009 | Bernstein et al. |
| 2009/0322636 A1 | 12/2009 | Brigham et al. |
| 2010/0056907 A1 | 3/2010 | Rappaport et al. |
| 2010/0081895 A1 | 4/2010 | Zand |
| 2010/0256462 A1 | 10/2010 | Rappaport et al. |
| 2010/0265159 A1 | 10/2010 | Ando et al. |
| 2010/0312301 A1 | 12/2010 | Stahmann |
| 2010/0321253 A1 | 12/2010 | Ayala Vazquez et al. |
| 2011/0004076 A1 | 1/2011 | Janna et al. |
| 2011/0022325 A1 | 1/2011 | Craddock et al. |
| 2011/0060215 A1 | 3/2011 | Tupin et al. |
| 2011/0068995 A1 | 3/2011 | Baliarda et al. |
| 2011/0130800 A1 | 6/2011 | Weinstein et al. |
| 2012/0029323 A1 | 2/2012 | Zhao |
| 2012/0098706 A1 | 4/2012 | Lin et al. |
| 2012/0104103 A1 | 5/2012 | Manzi |

FOREIGN PATENT DOCUMENTS

| | | |
|---|---|---|
| JP | 2008-515548 | 5/2008 |
| JP | 2008-530546 A | 7/2008 |
| JP | 2008-542759 A | 11/2008 |
| JP | 2010-512190 | 4/2010 |
| WO | WO 2006/130798 A2 | 12/2006 |
| WO | WO 2007/017861 A2 | 2/2007 |
| WO | WO 2008/070856 A2 | 6/2008 |
| WO | WO2008/148040 | 12/2008 |
| WO | WO2009/031149 | 3/2009 |
| WO | WO2009/031150 | 3/2009 |
| WO | WO2009/152625 | 12/2009 |
| WO | WO2011/067623 | 6/2011 |

OTHER PUBLICATIONS

Haude et al., Intracoronary Doppler—and Quantitative Coronary Angiography-Derived Predictors of Major Adverse Cardiac Events After Stent Implantation, Mar. 6, 2011, Circulation, vol. 103(9), pp. 1212-1217.

Beyer-Enke et al., Intra-arterial Doppler flowmetry in the superficial femoral artery following angioplasty., 2000, European Radiology, vol. 10, No. 4, pp. 642-649.

(56) References Cited

OTHER PUBLICATIONS

Ringer et al., Follow-up of Stented Carotid Arteries by Doppler Ultrasound, Sep. 2002, Neurosurgery, vol. 51, No. 3, pp. 639-643.
Kantarci et al., Follow-up of Extracranial Vertebral Artery Stents with Doppler Sonography., Sep. 2006, American Journal of Roentgenology, vol. 187, pp. 779,787.
Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, pp. 1172-1176.
Miura et al. "Time Domain Reflectometry: Measurement of Free Water in Normal Lung and Pulmonary Edema," American Journal of Physiology—Lung Physiology 276:1 (1999), pp. L207-L212.
International Search Report and Written Opinion, mailed Nov. 26, 2013 for Application No. PCT/IB2013/00663 filed Feb. 15, 2013.
International Patent Application PCT/IB2009/055438, "Locating Features in the Heart Using Radio Frequency Imaging", Filed on Dec. 1, 2009.
International Application PCT/IB2009/055438 Search Report dated Jul. 20, 2010.
International Application PCT/IB2010/054861 Search Report dated Apr. 5, 2011.
International Search Report for International Application No. PCT/IB2011/053244, date of mailing, Dec. 2, 2011.
Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.
Claron Technology Inc., "MicronTracker 3:A New Generation of Optical Trackers", Canada, 2009.
Immersion Corporation, "Immersion Introduces New 3D Digitizing Product-MicroScribe G2; Faster Data Transfer, USB Compatibility, New Industrial Design", Press Release, San Jose, USA, Jul. 1, 2002.
Polhemus, "Fastrak: The Fast and Easy Digital Tracker", USA, 2008.
Czum et al., "The Vascular Diagnostic Laboratory", The Heart & Vascular Institute Newsletter, vol. 1, USA, Winter, 2001.
Lal et al., "Duplex ultrasound velocity criteria for the stented carotid artery", Journal of Vascular Surgery, vol. 47, No. 1, pp. 63-73, Jan. 2008.
Larsson et al., "State Diagrams of the Heart—a New Approach to Describing Cardiac Mechanics", Cardiovascular Utrasound 7:22 (2009).
Bell et al., "A Low-Profile Achimedean Spiral Antenna Using an EBG Ground Plane", IEEE Antennas and Wireless Propagation Letters 3, pp. 223-226 (2004).
Supplementary European Search Report for Application No. EP 10834292.4 (PCT/IB2010/054861) dated Dec. 4, 2014.
Li, J.C. et al., "Microwave Imaging of Cerebral Edema", Proceedings of the IEEE, IEEE, NY, US, vol. 70, No. 5; May 1, 1982, pp. 523-524.
Guido Biffi Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.
Pedersen P C et al., "Microwave Reflection and Transmission Measurements for Pulmonary Diagnosis and Monitoring", IEEE Transactions on Biomedical Engineering, IEEE Service Center, Piscataway, NJ, US, vol. BME-19, No. 1, Jan. 1, 1978; pp. 40-48.
International Search Report for International Application No. PCT/IB2011/053246 date of mailing, Dec. 13, 2011.
Extended Search Report for European Application No. 11809360.8, date of mailing, Mar. 11, 2014.
Written Opinion of the International Searching Authority, mailed Jul. 20, 2010, for International Application No. PCT/IB2009/055438.
International Preliminary Report on Patentability, mailed Jun. 14, 2012, for International Application No. PCT/IB2009/055438.
Christine N. Paulson et al. "Ultra-wideband radar methods and techniques of medical sensing and imaging" Proceedings of Spie, vol. 6007, Nov. 9, 2005, p. 60070L.
S. I. Alekseev et al. "Human Skin permittivity determined by millimeter wave reflection measurements", Bioelectromagnetics, vol. 28, No. 5, Jul. 1, 2007, pp. 331-339.
Supplementary European Search Report and European Search Opinion, dated Jun. 13, 2013, for European Application No. 09851811.1.
Notice of Reasons for Rejection, mailed Apr. 28, 2014, for JP 2012-541588.
Notice of Reasons for Rejection, mailed Mar. 31, 2015, for JP 2012-541588.
Written Opinion of the International Searching Authority, mailed Dec. 2, 2011, for International Application No. PCT/IB2011/053244.
International Preliminary Report on Patentability, mailed Jan. 31, 2013, for International Application No. PCT/IB2011/053244.
Supplementary European Search Report and European Search Opinion, dated Feb. 26, 2014, for European Application No. 11809359.
International Search Report and Written Opinion, mailed Feb. 26, 2015, for International Application No. PCT/IL2014/050937.
Notice of Reasons for Rejection, mailed Apr. 17, 2015, for JP 2013-520273.

\* cited by examiner

LOCATING FEATURES IN THE HEART USING RADIO FREQUENCY IMAGING

CROSS-REFERENCE TO RELATED APPLICATION

This application is a 35 U.S.C. §371 national stage entry of PCT/IB2009/055438, which has an international filing date of Dec. 1, 2009 and which is a continuation-in-part of U.S. patent application Ser. No. 12/127,544 filed on May 27, 2008, which is assigned to the assignee of the present patent application, the contents of which are incorporated herein by reference in their entireties.

FIELD OF THE INVENTION

The present invention relates generally to methods and systems for medical diagnostic imaging, and specifically to radio frequency (RF)-based imaging.

BACKGROUND OF THE INVENTION

Narrowing of the coronary arteries due to atherosclerosis is commonly treated by implantation of a stent, using a catheter, to hold the artery open. In a large fraction of cases, however, the treated artery closes up again due to in-stent restenosis, necessitating further treatment. Accurate assessment of such restenosis generally requires re-catheterization. A number of non-invasive techniques have been proposed, such as in U.S. Pat. No. 6,729,336, in which an electromagnetic wave transmitter is used to excite a stent, and an acoustic sensor detects stent acoustic oscillations.

RF imaging is best known in the context of radar systems, but RF diagnostic imaging systems have also been developed for medical applications. For example, U.S. Patent Application Publication 2008/0169961, whose disclosure is incorporated herein by reference, describes computerized tomography using radar, which may be used for generating an image of living tissue. As another example, U.S. Pat. No. 7,454,242, whose disclosure is incorporated herein by reference, describes tissue-sensing adaptive radar imaging for breast tumor detection.

Various antenna designs have been proposed for RF imaging of body tissues. For example, U.S. Pat. No. 6,061,589, whose disclosure is incorporated herein by reference, describes a microwave antenna for use in a system for detecting an incipient tumor in living tissue, such as that of a human breast, in accordance with differences in relative dielectric characteristics. A composite Maltese Cross or bow-tie antenna construction is employed to irradiate the living tissue and to collect backscatter or other scatter returns.

SUMMARY

Embodiments of the present invention that are described hereinbelow provide improved devices and methods for detecting features inside a living body using RF imaging techniques. Although some of these embodiments are directed specifically to detection of features in the heart, and specifically in the coronary arteries, the principles of these embodiments may similarly be applied in imaging, detection and tracking of features elsewhere in the body.

There is therefore provided, in accordance with an embodiment of the present invention, diagnostic apparatus, including an antenna, which is configured to direct radio frequency (RF) electromagnetic waves into a living body and to generate signals responsively to the waves that are scattered from within the body. Processing circuitry is configured to process the signals so as to locate a feature in a blood vessel in the body.

In disclosed embodiments, the apparatus includes an ultrasound transducer, and the processing circuitry is configured to guide the ultrasound transducer to direct an ultrasonic beam toward the feature. In one embodiment, the feature located by the processing circuitry includes a stent, and the ultrasound transducer is configured to generate a Doppler signal responsively to a flow of blood through the stent.

Additionally or alternatively, the apparatus includes a tracking unit, which is configured to track respective coordinates of the antenna and of the ultrasound transducer, and the processing circuitry is configured to guide the ultrasound transducer responsively to the respective coordinates. The apparatus typically includes position transducers fixed respectively to the ultrasound transducer and to the antenna, wherein the tracking unit is configured to track the respective coordinates responsively to position signals exchanged between the position transducers and the tracking system.

Further additionally or alternatively, the apparatus includes a display, wherein the processing circuitry is configured to guide the ultrasound transducer by driving the display to present to an operator of the ultrasound transducer an indication of a direction in which the ultrasound transducer should be aimed.

In a disclosed embodiment, the blood vessel is a coronary artery. The processing circuitry may be configured to track a cyclical motion of the feature over multiple cycles of the heart.

Typically, the processing circuitry is configured to locate the feature responsively to a difference in a dielectric constant of the feature relative to surrounding tissue.

There is also provided, in accordance with an embodiment of the present invention, diagnostic apparatus, including an antenna, having a front surface configured to brought into contact with an outer surface of a living body so as to direct radio frequency (RF) electromagnetic waves into the body and to generate signals responsively to the waves that are scattered from within the body. A dielectric gel is adapted to be spread between the outer surface of the body and the front surface of the antenna. Processing circuitry is configured to process the signals so as to locate a feature in the body.

Typically, the body has a first dielectric constant, and the gel has a second dielectric constant that is chosen to match the first dielectric constant. In disclosed embodiments, the gel has a dielectric constant that is between 30 and 75. The gel may be adhesive.

In one embodiment, the gel is water-based and includes an additive selected from a group of additives consisting of an alcohol, a salt, a sugar, and glycerin. Alternatively, the gel includes silicone and an additive having a dielectric constant greater than 70.

There is additionally provided, in accordance with an embodiment of the present invention, diagnostic apparatus, including an antenna, which has a front surface and is configured to direct radio frequency (RF) electromagnetic waves from the front surface into a living body and to generate signals responsively to the waves that are scattered from within the body, and which includes an array of antenna elements, each antenna element including a planar element at the front surface of the antenna and a cavity behind the planar element. Processing circuitry is configured to process the signals so as to locate a feature in the body.

In disclosed embodiments, the front surface of the antenna includes a printed circuit board, and the planar element of each antenna element includes a conductive radiator printed on the printed circuit board. The printed circuit board may include multiple conductive vias surrounding the radiator for isolating the antenna elements from one another.

There is further provided, in accordance with an embodiment of the present invention, diagnostic apparatus, including an antenna, including an array of antenna elements, which are configured to direct radio frequency (RF) electromagnetic waves into a living body and to generate signals responsively to the waves that are scattered from within the body. Excitation circuitry is coupled to apply a RF excitation waveform at multiple different frequencies to different transmitting antenna elements, selected from the array, according to a predetermined temporal pattern. Processing circuitry is coupled to receive the signals from different receiving antenna elements, selected from the array, and to process the signals at the different frequencies due to the different transmitting and receiving antenna elements so as to locate a feature in the body.

In some embodiments, the excitation circuitry includes a driver circuit, which is configured to generate the RF excitation waveform with a variable frequency, and a switching matrix, which is configured to select sets of the antenna elements in alternation, each set including at least one transmitting antenna element and one receiving antenna element, and for each selected set, to couple the driver circuit to excite the at least one transmitting antenna element at a selected frequency while coupling the processing circuitry to receive the signals from the at least one receiving antenna element. In a disclosed embodiment, the driver circuit and the switching matrix are coupled to select pairs of one transmitting antenna element and one receiving antenna element, and to excite the transmitting antenna in each pair at each of a plurality of frequencies in accordance with the predetermined temporal pattern.

In some embodiments, the apparatus includes a signal conditioning unit, which is configured to cancel a background component of the signals that arises from direct coupling between the transmitting and receiving antenna elements before the processing circuitry receives the signals. The signal conditioning unit may include an amplitude and phase modulator, which is coupled to receive the RF excitation waveform from the driver circuit, to modify a phase and amplitude of the received waveform so as to generate an anti-phased signal matching the background component, and to add the anti-phased signal to a signal received from the at least one receiving antenna element in order to cancel the background component.

In disclosed embodiments, the processing circuitry is configured to transform the signals received at the different frequencies due to the different transmitting and receiving antenna elements into a three-dimensional (3D) image, and to process the 3D image in order to find a location of the feature. In one embodiment, the processing circuitry is configured to compute a weighted sum of the signals received at the different frequencies due to the different transmitting and receiving antenna elements, using respective weights provided for a plurality of voxels in the 3D image, to determine values of the voxels in the 3D image.

There is moreover provided, in accordance with an embodiment of the present invention, a method for diagnosis, including directing radio frequency (RF) electromagnetic waves into a living body and generating signals responsively to the waves that are scattered from within the body. The signals are processed so as to locate a feature in a blood vessel in the body.

There is furthermore provided, in accordance with an embodiment of the present invention, a method for diagnosis, including spreading a dielectric gel between an outer surface of a living body and a front surface of an antenna. The front surface of the antenna is brought into contact, via the dielectric gel, with the outer surface of the living body so as to direct radio frequency (RF) electromagnetic waves into the body and to generate signals in the antenna responsively to the waves that are scattered from within the body. The signals are processed so as to locate a feature in the body.

There is also provided, in accordance with an embodiment of the present invention, a method for diagnosis, including providing an antenna, which has a front surface and which includes an array of antenna elements, each antenna element including a planar element at the front surface of the antenna and a cavity behind the planar element. Radio frequency (RF) electromagnetic waves are directed from the antenna elements via the front surface of the antenna into a living body and generating signals, using the antenna elements, responsively to the waves that are scattered from within the body. The signals are processed so as to locate a feature in the body.

There is additionally provided, in accordance with an embodiment of the present invention, a method for diagnosis, including defining a temporal pattern specifying a sequence of multiple different frequencies and spatial channels associated with an array of antenna elements. Radio frequency (RF) electromagnetic waves are directed at the multiple different frequencies into a living body from multiple different transmitting antenna elements that are selected from the array in accordance with the temporal pattern. Signals are generated responsively to the waves that are scattered from within the body and are received at multiple different receiving antenna elements that are selected from the array in accordance with the temporal pattern. The signals from the different receiving antenna elements at the different frequencies are processed so as to locate a feature in the body.

The present invention will be more fully understood from the following detailed description of the embodiments thereof, taken together with the drawings in which:

DETAILED DESCRIPTION OF EMBODIMENTS

Overview

Figure 1:
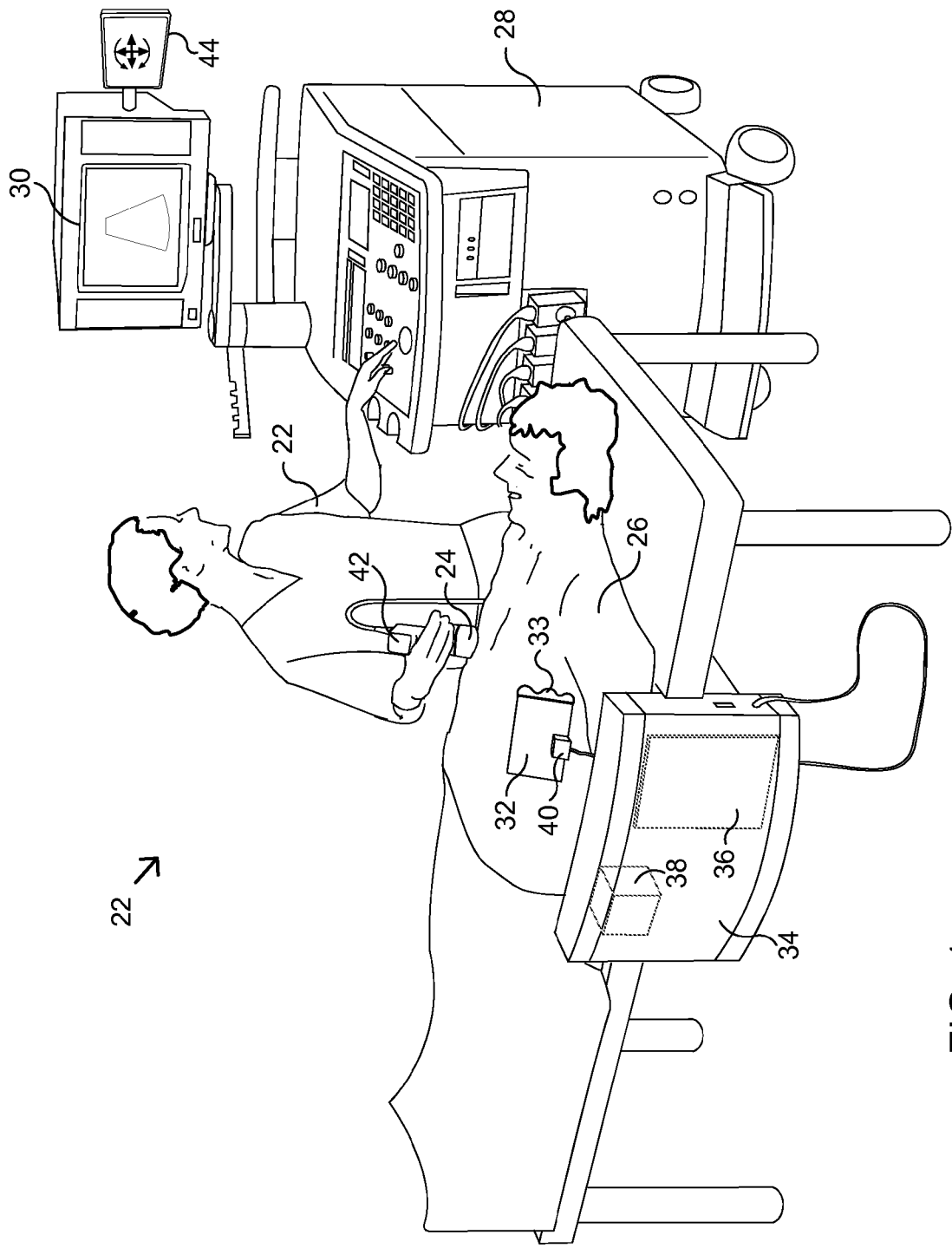
FIG. 1 is a schematic, pictorial illustration of a system for tracking and assessment of a feature in a human body, in accordance with an embodiment of the present invention.

Embodiments of the present invention that are described hereinbelow use radar imaging techniques to identify and locate features in the body. Features are thus identified based on the difference in their complex dielectric constant (referring to both permittivity and conductivity) relative to the dielectric constant of the surrounding tissue. These techniques are particularly useful in detecting and tracking metal objects in the body, but they may also be used to locate features of other kinds, including both introduced objects, such as plastic objects, and naturally-occurring features, such as calcifications, and even pockets of air or other gases. The term "feature," as used in the context of the present patent application and in the claims, should therefore be understood as referring to any item or location in the body having a distinct dielectric constant.

Some embodiments of the present invention are directed to locating features in the heart, and particularly in the coronary blood vessels. In these embodiments, an antenna directs RF electromagnetic waves toward the heart and receives the waves that are scattered from within the body. Processing circuitry processes the signals generated by the antenna due to the received waves in order to locate the feature or features of interest, and possibly to track the movement of such features over the course of the heart cycle.

The radar-based location of a feature may be used in guiding the beam of an ultrasound transducer toward the feature. In one such embodiment, the antenna and processing circuitry find the location of a stent in an artery and guide the ultrasound transducer to direct its beam toward the stent. The ultrasound transducer may operate in Doppler mode in order to measure the flow of blood through the stent and thus non-invasively assess possible restenosis in the stent.

In the embodiments that are described hereinbelow, the antenna comprises an array of antenna elements, with a front surface that is brought into contact with the outer surface (i.e., the skin) of the patient's body. A dielectric gel may be spread between the body surface and the front surface of the antenna in order to match the dielectric constants and thus improve the penetration of the RF waves into the body. Additionally or alternatively, the antenna elements may comprise a cavity and possibly other features to enhance the efficiency of coupling of electromagnetic energy from the antenna elements into the body while reducing loss and crosstalk between the elements.

In the disclosed embodiments, excitation circuitry applies a RF excitation waveform at multiple different frequencies to different transmitting antenna elements in the array. Meanwhile, the processing circuitry receives signals from different receiving antenna elements. The selection of transmitting and receiving antennas, as well as the selection of excitation frequency, follows a predetermined temporal pattern, which may be implemented by a switching matrix connected to the antenna elements.

As a result of this scheme of excitation and reception, the processing circuitry receives and processes signals from multiple spatial channels (corresponding to different pairs of antennas) at multiple different frequencies for each channel. Taken together in the time domain, these multi-frequency signals are equivalent to short pulses of RF energy. To reconstruct a three-dimensional (3D) image of the interior of the body and find the location of a feature or features, the processing circuitry applies a spatial transform to the set of received signals. The transform may, for example, comprise an inverse spherical Radon transform or an algebraic approximation of such a transform.

Despite measures that are taken to reduce coupling between antenna elements within the array, this sort of direct coupling still generates a strong background component, which tends to mask the signals due to scattered waves from the body. (The term "direct coupling," as used in the context of the present patent application and in the claims, refers to short-range passage of RF waves between antenna elements by paths other than through the region of interest in the patient's body, including coupling that occurs within the array and near-field reflections.) In order to reduce this masking and enhance the dynamic range of the signals, in some embodiments a signal conditioning unit is used to adaptively cancel the background component out of the signals that are passed to the processing circuitry. To improve visibility of moving features, such as features in the heart, the signal conditioning unit or another element of the processing circuitry may even be configured to cancel all parts of the signals that do not vary over time.

System Description

FIG. 1 is a schematic, pictorial illustration of a system 20 for tracking and assessment of a feature in a body of a patient 26, in accordance with an embodiment of the present invention. In this embodiment, an operator 22, such as a physician, directs an ultrasonic beam from an ultrasound transducer 24 into the chest of patient 26. The probe containing transducer 24 operates in Doppler mode, as is known in the art, in order to measure the velocity of blood flowing through a coronary artery of the patient, and specifically through a stent (not shown) that is implanted in one of the patient's coronary arteries. A console 28 drives transducer 24 and processes the signals that are output by the transducer in order to extract the Doppler information and displays the results on a monitor 30. The operator steers the probe toward the location of the stent under guidance from system 20, as explained in detail hereinbelow.

Aiming the ultrasound probe correctly under these circumstances is difficult: The stent is small and is typically embedded in clutter in the ultrasound image due to other anatomical features; and the stent and surrounding features of the heart are in continual motion. Therefore, system 20 uses radar imaging in order to find the location of the stent and guide operator 22. For this purpose, an antenna 32 directs RF waves into the patient's chest. For good dielectric matching, in order to enhance the penetration of the RF waves into the body, a layer of a dielectric gel 33 is spread between the front surface of the antenna and the patient's skin. The gel may also have adhesive qualities, in order to aid in holding the antenna in place during the procedure.

Typically, gel 33 has a dielectric constant that is between 30 and 75. This value defines the effective dielectric constant of the antenna in its near-field. It is chosen to be close to the effective dielectric constant of the tissue layers in the path to the target region in the body. The desired dielectric constant may be achieved by increasing or decreasing the concentration of certain additives in the gel. For example, if a water-based gel is used, the additive may be an alcohol (such as ethanol), salt, sugar, or glycerin. Alternatively, a silicone gel may be used with an additive such as barium, having generally a dielectric constant greater than 70.

Antenna 32 is coupled by a cable or wireless link to a radar control unit 34. The control unit comprises processing circuitry 36, which drives the antenna to emit the RF waves into the body and processes the signals generated by the antenna due to reception of scattered waves from the body. Based on the received signals, circuitry 36 forms a 3D radar image of the interior of the body, and specifically, in the present embodiment, finds the location of the stent. These functions of circuitry 36 are described in detail hereinbelow.

In order to guide the direction of ultrasound transducer 24, the position coordinates (location and orientation) of the transducer and of antenna 32 are registered in a common coordinate frame. For this purpose, system 20 includes a tracking subsystem, comprising a tracking transmitter 38, which generates a field that is detected by sensors 40 and 42 on the antenna and on the ultrasound transducer, respectively. Transmitter 38 may, for example, generate a magnetic field, and sensors 40 and 42 may be magnetic sensors, as in the trakSTAR™ system distributed by Ascension Technology Corporation (Milton, Vt.). Alternatively, sensors 40 and 42 may be replaced by transmitting elements, which generate fields that are detected by a fixed sensor.

Further alternatively, other types of tracking devices may be used, such as optical, ultrasonic or mechanical position sensing devices, as are known in the art. For the sake of generality, the term "position transducer" is used herein to refer to the elements that are attached to ultrasound transducer 24 and antenna 32, such as sensors 40 and 42, for the purpose of finding their coordinates, regardless of the specific choice of position sensing technology. Additionally or alternatively, ultrasonic transducer 24 and antenna 32 may be mechanically fixed in a common frame of reference. A variety of alternative configurations are described in the above-mentioned U.S. patent application Ser. No. 12/127,544 and may similarly be used with the elements of system 20.

In the system configuration shown in FIG. 1, sensors 40 and 42 output signals to processing circuitry 36. The processing circuitry processes the signals to find location and orientation coordinates of the sensors, and hence of antenna 32 and transducer 42, in a common coordinate frame. Based on these coordinates, processing circuitry 36 registers the ultrasonic images formed by transducer 24 with the radar images formed by antenna 32. The processing circuitry finds the location of the stent in the radar image, and may also estimate its orientation. On this basis, the circuitry guides operator 22 to aim transducer 24 toward the stent along the stent axis, i.e., along the direction of blood flow, in order to maximize the Doppler component in the ultrasound signals. For this purpose, the processing circuitry drives a guidance display 44, which indicates to the operator how to aim the ultrasound transducer toward the target.

In an alternative embodiment (not shown in the figures), ultrasound transducer 24 may be held and manipulated by a robot arm, which is guided automatically by processing circuitry to aim the transducer in the desired direction.

Although FIG. 1 shows a particular type of antenna and mode of coupling the antenna to the patient's body, other antenna types and configurations may also be used for the purposes described herein. For example, the antenna may mounted in a cushion below the patient's back, in a wearable element that fits over the patient's body, or in any other suitable mount. Some alternative configurations of this sort are shown in the above-mentioned U.S. patent application Ser. No. 12/127,544.

Figure 2:
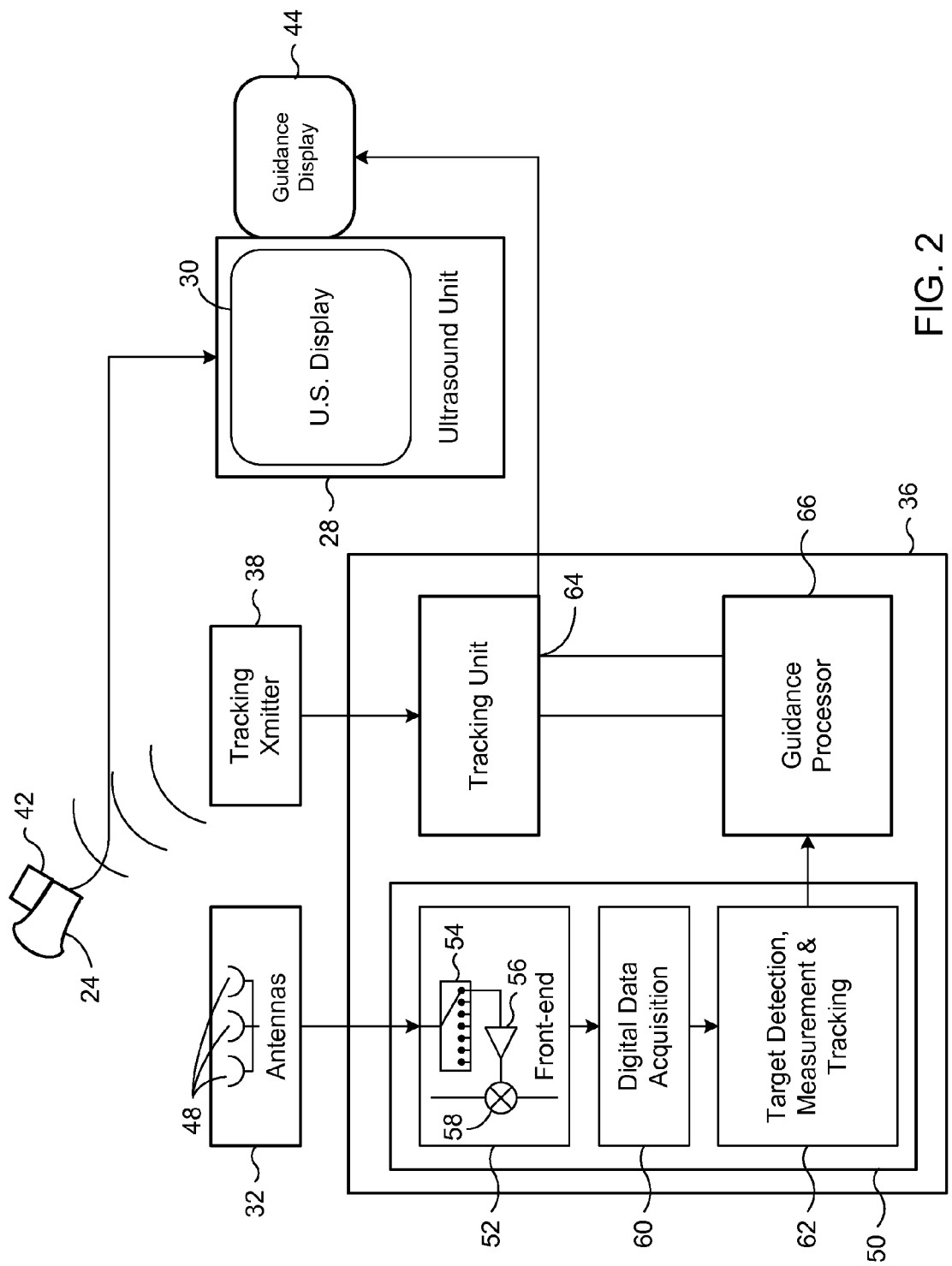
FIG. 2 is a block diagram that schematically shows elements of a system for tracking and assessment of a feature in a human body, in accordance with an embodiment of the present invention.

FIG. 2 is a block diagram that schematically shows key elements of system 20, and particularly of processing circuitry 36, in accordance with an embodiment of the present invention. Some of these elements are described in greater detail hereinbelow. Antenna 32 is driven by and outputs signals to a feature detection subsystem 50. The antenna typically comprises an array of antenna elements 48, which are connected to a switching matrix 54 in a front end 52 of subsystem 50. The switching matrix selects different sets of the antennas to transmit and receive signals at different, respective times and frequencies, in a predetermined temporal pattern. Typically, the sets comprise pairs of antennas— one transmitting and one receiving—although other groupings may also be used. The pattern of antenna control is described in detail hereinbelow.

A driver circuit 58 generates signals, at multiple different frequencies, for exciting the transmitting antennas and demodulates the signals received by the receiving antennas. Typically, the signals are in the range of about 400 MHz to about 4 GHz, although higher and lower frequencies outside this range may also be used. A signal conditioning unit 56 between the driver circuit and switching matrix 54 amplifies the outgoing and the incoming signals and also cancels background components in the received signals. This functionality is also described below.

Front end 52 outputs the demodulated received signals (as intermediate-frequency or baseband signals) to a digital data acquisition unit 60, which samples and digitizes the signals. Unit 60 typically comprises a high-resolution analog/digital converter, such as a 14-bit converter, with suitable sampling circuits as are known in the art.

A target detection, measurement and tracking unit 62 receives and processes the digital samples. Unit 62, as described in detail hereinbelow, processes the sampled signals in order to generate a 3D radar image of the interior of the chest of patient 26. Within this image, elements having a dielectric constant that is different from that of the surrounding tissue, such as a metal stent in a coronary artery, stand out. On this basis, unit 62 identifies and measures the location coordinates of the stent relative to antenna 32.

Since the heart is in constant motion, unit 62 may also track and model the motion of the stent in order to more precisely guide ultrasound transducer 24. The direction of motion of the stent during the heart cycle also gives an indication of the direction of the stent axis (along which the ultrasound transducer should be aimed): Since the axis of the stent is oriented along the coronary artery in which the stent is implanted, and the coronary artery runs along the heart wall, the stent axis will typically be perpendicular to the direction of motion of the heart wall, and hence to the axis of motion of the stent in the radar image. As noted above, operator 22 is guided to aim ultrasound transducer 24 toward the stent in a direction along, or at least close to, the stent axis.

Although the present embodiment relates specifically to identification and tracking of a stent, the techniques and circuits that are described here may be used, by the same token, in locating and tracking other features in the coronary blood vessels, such as calcifications, as well as features elsewhere in the body.

A tracking unit 64 communicates with tracking transmitter 38 and receives position signals from position sensors 40 and 42. The tracking unit processes these signals in order to compute the coordinates of ultrasound transducer 24 and antenna 32 in the frame of reference of transmitter 38. The tracking unit may be a commercially-available device, such as in the above-mentioned FASTRAK system.

A guidance processor 66 receives the position (location and orientation) coordinates from tracking unit 64 and the position coordinates of the stent from feature detection subsystem 50. Guidance processor 66 registers the coordinates of the stent in the coordinate frame of the tracking unit or, equivalently, registers the coordinates of ultrasound transducer 24 in the coordinate frame of antenna 32, in which the stent coordinates have been found. The guidance processor is then able to compute the geometrical skew and offset between the present viewing axis of the ultrasound transducer and the desired viewing axis, which will intercept the stent along (or close to) the stent axis. Based on the computed skew and offset, the guidance processor may drive guidance display 44 to show operator 22 the required correction. For this purpose, the guidance display may show, for example, target crosshairs and directional arrows, or any other suitable sort of directional indication. Alternatively, console 28 may use the computed skew in adjusting the Doppler velocity readings to account for the angle of measurement relative to the flow.

Processing circuitry 36 typically comprises a combination of dedicated hardware circuits (such as in front end 52 and digital data acquisition unit 60) and programmable components. The front end circuits are described in detail hereinbelow. Target detection, measurement and tracking unit 62 and guidance processor 66 typically comprise programmable processors, such as a general-purpose microprocessor or a digital signal processor, which are programmed in software to carry out the functions that are described herein. Alternatively or additionally, these elements of circuitry 36 may comprise dedicated or programmable digital logic units such as an application-specific integrated circuit (ASIC) or a field-programmable gate array (FPGA). Although units 62 and 64 and processor 66 are shown, for the sake of conceptual clarity, as separate functional blocks, in practice at least some of the functions of these different blocks may be carried out by a single processor. Alternatively, the functions of a given block may be divided up among two or more separate processors.

Antenna Design and Operation

Figure 3:
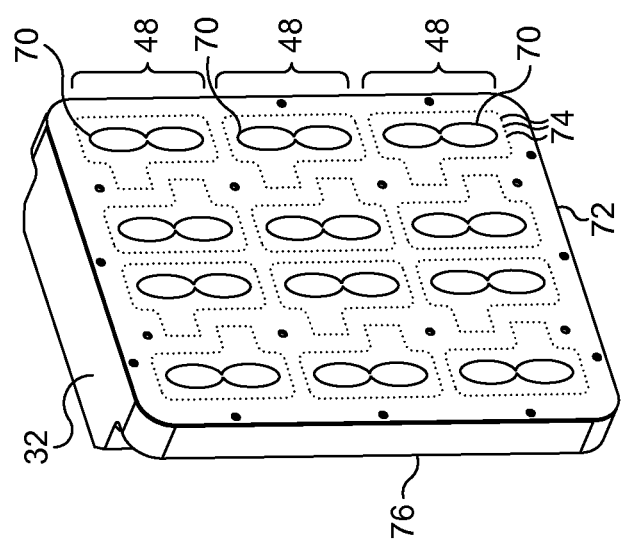
FIG. 3 is a schematic, pictorial illustration of an antenna array, in accordance with an embodiment of the present invention.

FIG. 3 is a schematic, pictorial illustration of antenna 32, in accordance with an embodiment of the present invention. Antenna 32 is a planar ultra-wideband, unidirectional antenna, comprising an array of antenna elements 48. The antenna is designed for high-permittivity surroundings, enabling transmission and reception of ultra-wideband signals to and from the human body with minimal loss. In the pictured embodiment, the antenna comprises twelve antenna elements 48, which are spread in a rectangular plane to allow Cartesian acquisition of an image. Alternatively, the antenna may comprise a larger or smaller number of antenna elements, in a rectangular or non-rectangular array.

Each antenna element 48 comprises a planar element comprising a conductive radiator 70, which is printed on a circuit board 72. This circuit board serves as the front surface of antenna, which is brought into contact with the patient's body. Circuit board 72 comprises multiple conductive vias 74 surrounding each radiator 70 for isolating antenna elements 48 from one another. The antenna elements are enclosed from behind by a case 76.

Figure 4:
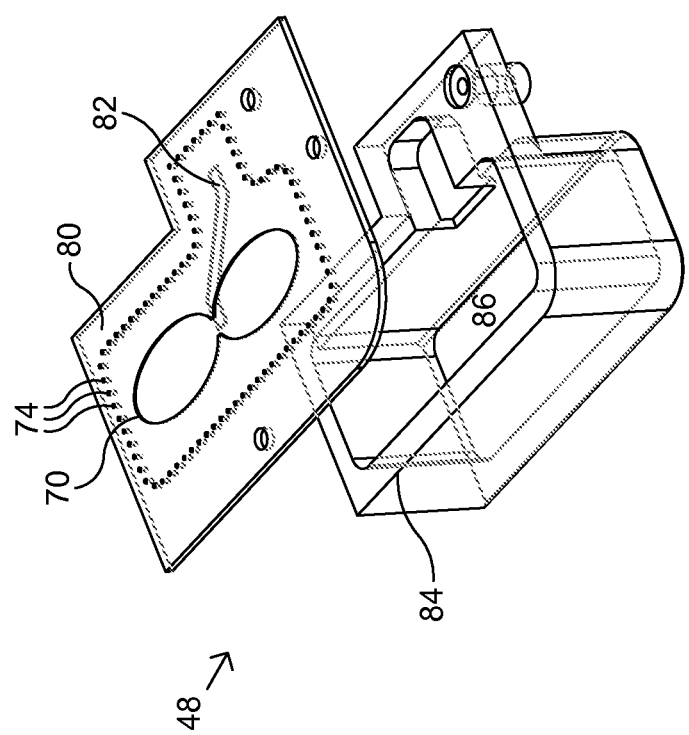
FIG. 4 is a schematic, exploded view of an antenna element, in accordance with an embodiment of the present invention.

FIG. 4 is a schematic, exploded view of one of antenna elements 48, in accordance with an embodiment of the present invention. Each antenna element is constructed as an ellipse-shaped slotted antenna, excited electrically at its center feed point. Circuit board 72 comprises a dielectric substrate, such as an FR4 laminate, with a component (front) side that includes radiator 70 and a ground plane 80. The radiator shape is optimized with an elliptical template to maintain a low voltage standing wave ratio (VSWR), with high antenna gain and flatness at boresight. This flatness assures good coverage of the entire region of interest (ROI) in the patient's body with constant antenna gain.

The printed (rear) side of board 72 includes an excitation transmission line 82 feeding the center point of radiator 70 through a conductive via. Transmission line 82 comprises a fifty-ohm microstrip, with a micro-miniature coaxial (MMCX) connector (not shown) for connecting to front end 50. Alternatively, other types of radiator shapes and feed lines may be used.

A conductive cavity 84 is attached to the component side of board 72 behind each radiator 70 in order to reduce antenna reverberations from back-lobe scattering and to increase the overall gain. (Antenna element 48 as shown in FIG. 4 has a nominal gain of 7 dBi at boresight.) Cavity 84 comprises a hollow waveguide 86, with dimensions designed such that the cutoff frequency of the lowest propagating mode (TE10) in the waveguide is higher than the upper band frequency limit of antenna 32, i.e., $$f_{cutoff} = \frac{C_0/\sqrt{\varepsilon_r}}{2a},$$

wherein $C_0$ is the speed of light, $\varepsilon_r$ is the permittivity of the interior of the waveguide, and $a$ is the largest transverse dimension of the waveguide. In the present example, with a frequency limit of 4 GHz, the depth of waveguide 86 is 15 mm. The waveguide creates an imaginary characteristic impedance, causing back-lobe radiation from radiator 70 to reflect from the cavity in phase with the back-lobe waves. This reflection enhances the external buffering of the antenna and attenuates non-TE and TM modes, and therefore reduces interference and noise.

Cross-coupling between antenna elements 48 can cause interference, which reduces the dynamic range and may saturate the receiver circuits. This cross-coupling is reduced in antenna 32 by appropriately setting the distance between the antenna elements in the array and by surrounding radiators 70 with conductive vias 74, as noted above. The vias serve as an electric wall that prevents internal waves from traveling between elements. They also create a conductive continuity between ground plane 80 on the component side of board 72 and the top conductive transverse plane of waveguide 86 located on the print side.

Antenna 32 is sealed against liquids and gels, thus preventing unwanted materials from reaching the print side and cavities of the antenna elements. Case 76, including cavities 84, can be constructed from a molded plastic with a suitable conducting coating. Additionally or alternatively, the antenna elements may be printed on the molded plastic after coating. Although switching matrix 54 is shown and described herein as a part of processing circuitry 36, it may alternatively be incorporated into antenna 32 or mounted adjacent to the antenna, thereby performing the switching alongside the patient and reducing the weight and rigidity of the cable from the antenna to control unit 34.

Although antenna 32 is shown here as a unitary assembly containing antenna elements 48, the antenna elements (of similar design to that shown in FIG. 4) may alternatively be used singly or as dual- or multi-element panels, which can be attached to different body locations. Multiple position sensors can be used to compute and register the respective positions of the antenna elements. In such embodiments, system 20 may be configured to measure and analyze both waves reflected from the region of interest of the body and waves transmitted through the region and scattered by the target.

Signal Switching and Processing

Figure 5:
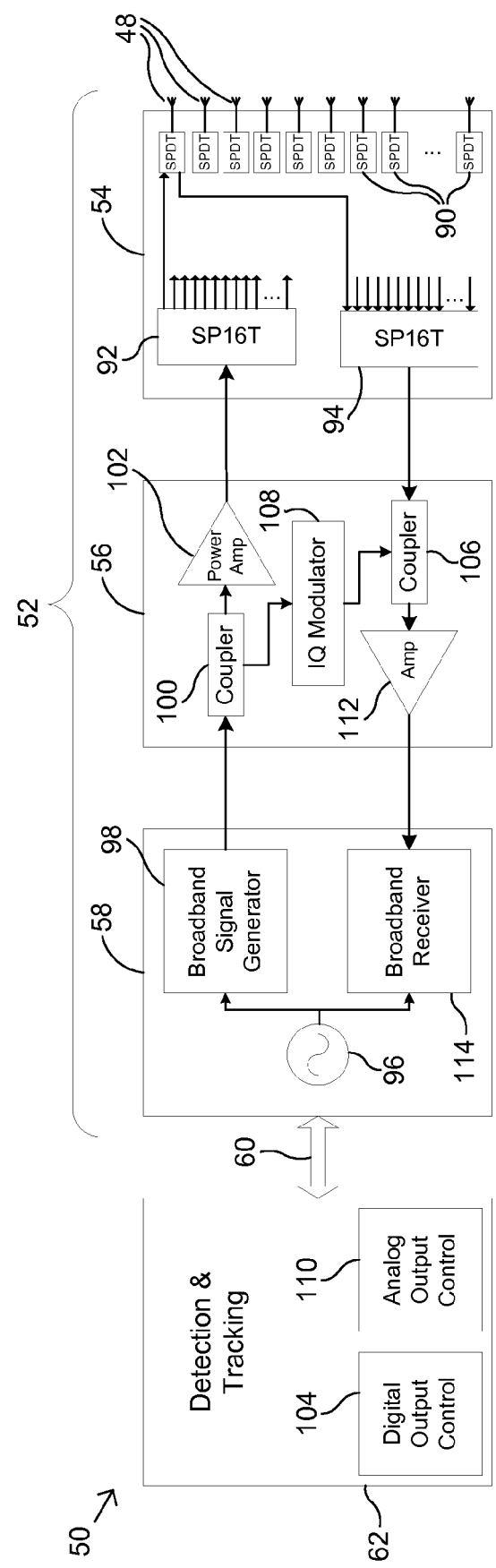
FIG. 5 is a block diagram that schematically illustrates a feature detection subsystem, in accordance with an embodiment of the present invention.

FIG. 5 is a block diagram that schematically shows details of feature detection subsystem 50, in accordance with an embodiment of the present invention. As noted earlier, switching matrix 54 connects antenna elements 48 to the other circuits of front end 52. Each antenna element connects to a respective single-pole double-throw (SPDT) switch 90, which determines whether the switch is to transmit or to receive waves at any given time. The transmit antenna element is selected, from among the multiple antenna elements, by a transmit switch 92, while the receive antenna element is selected by a receive switch 94. The switching matrix thus permits any pair of the antenna elements to be selected as the transmitter and receiver at any given time.

Switching matrix 54 is designed for high isolation between channels, typically better than 40 dB over the entire frequency range of antenna 32. Switches 90, 92 and 94 are digitally controlled by a digital output control module 104 and allow fast (non-mechanical) switching. This fast switching is required in order to allow the entire waveform sequence of different antenna pairs and frequencies to be completed in a short frame time, as described hereinbelow. For this purpose, matrix 54 is typically configured to achieve a switching time of less than 1 µs.

Figure 6:
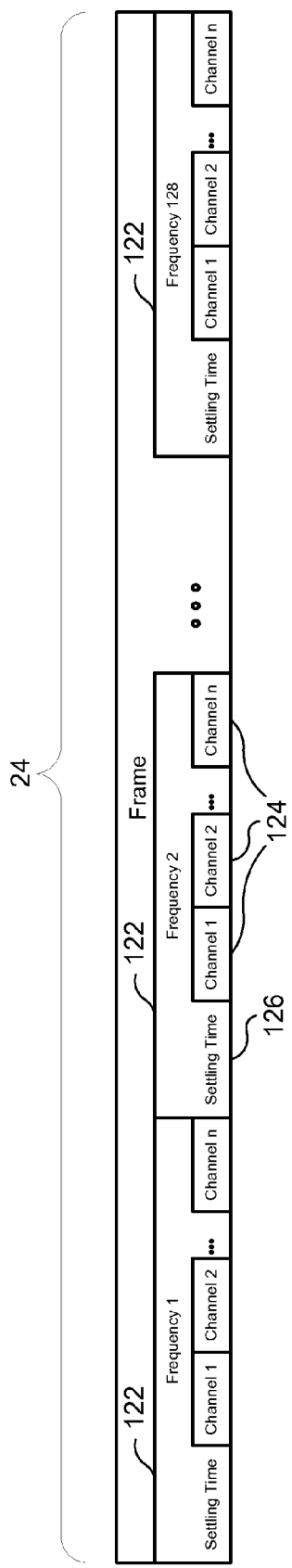
FIG. 6 is a timing diagram that schematically illustrates an excitation pattern that is applied to an antenna array, in accordance with an embodiment of the present invention.

Driver circuit 58 comprises a broadband signal generator 98, which generates the RF excitation waveform to drive the transmitting antenna elements, and a receiver 114, which receives and demodulates the signals generated by the receiving antenna elements. Signal generator 98 and receiver 114 are both synchronized and sweep their frequencies according to a predefined frequency plan, which is shown in FIG. 6, based on a shared local oscillator 96. The frequency plan specifies the frequencies and power levels to be generated by the signal generator, in synchronization with an external trigger. The driving waveform entering signal conditioning unit 56 from signal generator 98 is sampled by a broadband coupler 100, amplified by a power amplifier 102 according to the required transmit power level, and transferred to switching matrix 54.

Receiver 114 is a tuned super-heterodyne receiver, which is able to adjust its bandwidth and gain according to the received signal. The receiver demodulates the received signals coherently, in synchronization with local oscillator 96, in order to extract both the amplitude and the phase of the signals. The complex ratio between the transmitted and received signals, as measured by detection, measurement and tracking unit 62 for each antenna pair at each selected frequency, indicates the frequency response along corresponding paths through the region of interest. This region includes the chest, thoracic cavity, beating heart and the stent itself.

Despite the measures described above for reducing coupling between different antenna elements 48 in antenna 32, the signals received from antenna 32 by signal conditioning unit 56 may still include a strong background component due to the direct coupling between the transmitting and receiving antenna elements. This background component raises the noise level due to transmitter nonlinearity and impurities in the transmitted signal and can even cause receiver 114 to saturate. It is therefore desirable to reduce the level of the background component that reaches the receiver in order to enhance the dynamic range of the radar image.

For this purpose, signal conditioning unit 56 comprises an amplitude and phase modulator, referred to here as an IQ modulator 108, which receives the sampled RF excitation waveform from coupler 100. The IQ modulator modifies the phase and amplitude of the sampled signal, under the control of an analog output control module 110, so as to generate an anti-phased signal matching the background component that is to be canceled. The amplitude and phase values of IQ modulator 108 are periodically updated and are then kept constant per frequency and per channel until coupling values change significantly and need updating. In other words, IQ modulator 108 outputs a signal that is equal in amplitude to the background component but 180° out of phase. A coupler 106 adds this anti-phased signal to the received signal from switching matrix 54 and thus cancels the background component without degrading the actual radar signal from the body. An amplifier 112 amplifies the signal following background cancellation for input to receiver 114.

FIG. 6 is a timing diagram that schematically illustrates a temporal excitation pattern that front end 52 applies to antenna 32, in accordance with an embodiment of the present invention. The front end generates a sequence of frames 120. Each time a radar measurement is triggered (ten times per second, for example), the frame defines a sweep of the excitation signal both in frequency and over spatial channels (antenna pairs). Each frame 120 comprises multiple frequency sub-frames 122 according to the number of frequencies to be used in image reconstruction. In the example shown in FIG. 6, there are 128 such sub-frames, each lasting 750 µs. The frequencies in this example, as noted above, span the range between 400 MHz and 4 GHz.

Each sub-frame 122 begins with a settling time 126 (typically a few hundred microseconds) for locking the amplitude and phase of signal generator 98. Following this initial delay, switching matrix 54 selects different channels 124 in sequence. Each channel uses one transmitting antenna element and one receiving antenna element, up to a total of n channels (for example, one hundred such channels in the example shown in FIG. 6, each open for 5 µs). During each channel period, detection, measurement and tracking unit 62 collects samples of the received signal from receiver 114 for subsequent use in multi-frequency/multi-channel radar image reconstruction.

In alternative embodiments (not shown in the figures), other sorts of channel configurations may be used. For example, in monostatic configurations, a selected antenna element may serve as both transmitter and receiver, as opposed to bistatic or multistatic configurations, in which each antenna either transmits or receives. As another option, antenna elements may simply transmit and receive broadband RF pulses, rather than multiple narrowband pulses as in the embodiment described above.

Method of Operation

Based on the collected samples of the received signals, detection, measurement and tracking unit 62 detects small reflecting volumes within the region of interest (ROI) in the patient's body. As noted above, the corresponding reflections arise at the boundaries of media having different dielectric properties. The information provided by coherent detection of the signals over the broad range of frequencies covered in each frame is equivalent mathematically to the temporal information that would be provided by reflection of a single short pulse. The locations of the reflectors may be found by integrating over the propagation paths of the reflected waves, using an inverse spherical Radon transformation, for example.

In an embodiment of the present invention, detection, measurement and tracking unit 62 implements a first-order approximation of the inverse spherical Radon transform: For each voxel (x, y, z) in the ROI and for each frequency f and pair of antenna elements, a complex weight W(x,y,z,f,pair) is pre-calculated, either using an empirical calibration procedure or mathematical modeling. The weight is, in effect, the normalized complex amplitude (with conjugated phase) of the reflection that would be received at the receiving antenna in the pair from a point object at location (x,y,z) when irradiated by the transmitting antenna with a wave of frequency f. Because the body tissue through which the waves propagate is inhomogeneous, the weights may be adjusted, either empirically or by model calculation, to account for the specific tissue layers (skin, fat, muscle, lungs, etc.) through which the waves pass.

The set of weights thus derived defines a sort of matched filter. Detection, measurement and tracking unit 62 applies this filter to the matrix of complex signals Sig(f,pair) that it receives in any given frame in order to compute the reflection intensity V for each voxel, as a weighted sum over the received signals:

$$V(x, y, z) = \sum_{pair} \sum_{f} W(x, y, z, \text{pair}, f) \cdot Sig(\text{pair}, f) \quad (1)$$

The inventors have found that this simplified approximation of the inverse spherical Radon transform is both robust and computationally efficient.

Figure 7:
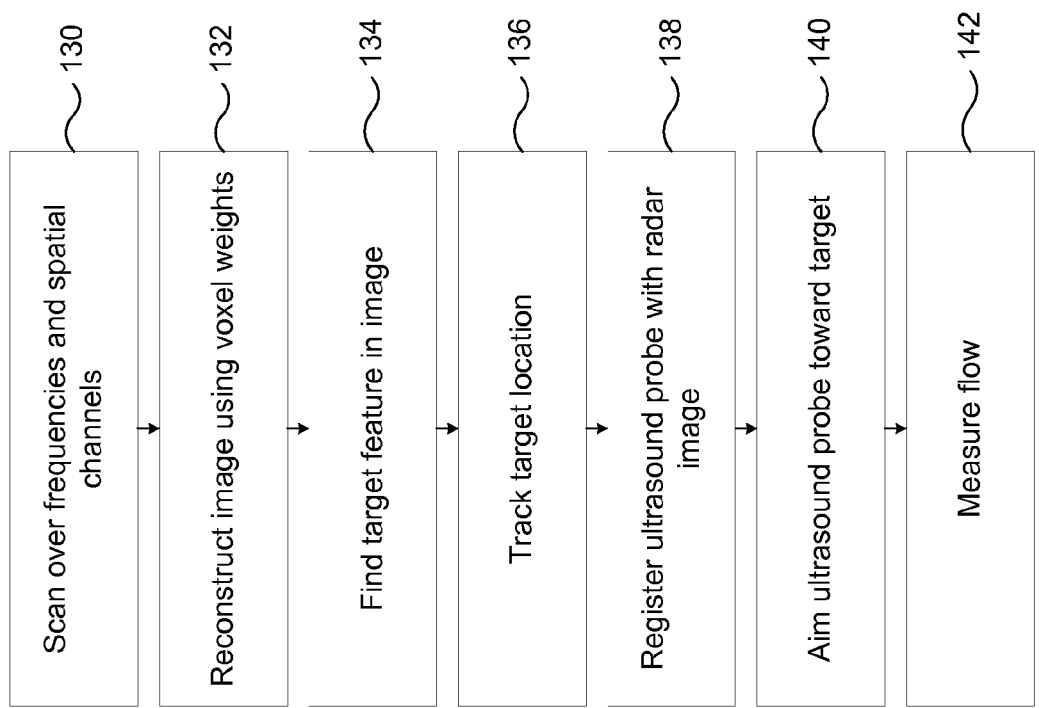
FIG. 7 is a flow chart that schematically illustrates a method for measuring blood flow through a stent, in accordance with an embodiment of the present invention.

FIG. 7 is a flow chart that schematically illustrates a method for measuring blood flow through a stent, in accordance with an embodiment of the present invention. The method is described hereinbelow, for the sake of clarity, with reference to the elements of system 20 that have been described above, but the same techniques may similarly be implemented in other system configurations. Furthermore, the elements of this method that relate to locating the stent in the body of patient 26 may likewise be applied, mutatis mutandis, for locating other features, both natural and artificial, in the coronary blood vessels, as well as elsewhere in the body.

Front end 52 drives antenna 32 to emit and receive RF waves over multiple frequencies and spatial channels (antenna pairs), at a scanning step 130, as described above. Detection, measurement and tracking unit 62 collects samples of the received signals and applies the weights defined in equation (1) to transform the signal values to voxel intensities, at an image reconstruction step 132. To improve the clarity of the image, the processing circuitry may apply additional image processing operations, such as subtracting the mean voxel value from all voxels in the image. The mean value may be smoothed over multiple successive images using a recursive filter. Unit 62 then identifies the coordinates of the target feature, i.e., the stent or another strong reflector, in the 3D image, at a target identification step 134.

Features in the coronary arteries (or elsewhere in the heart), such as the stent, move regularly with the heart rhythm, as well as with chest movement due to respiration. In order to guide the ultrasound transducer, detection, measurement and tracking unit 62 tracks the motion of the target in the successive images, at a target tracking step 136. For example, unit 62 may apply a Kalman filter, as is known in the art, to estimate the motion trajectory of the target.

Guidance processor 66 registers the coordinates of ultrasound transducer 24 with antenna 32, at a coordinate registration step 138. The processor uses the position coordinates provided by position sensors 40 and 42 at this step, as explained above. Based on these coordinates, the processor registers the ultrasound beam in the coordinate frame of the 3D image that was reconstructed at step 132.

Guidance processor 66 drives guidance display 44 to guide operator 22 in aiming the ultrasound beam toward the target, at an aiming step 140. It could be possible but would probably be impractical for a human operator, to move ultrasound transducer 24 continually back and forth in synchronism with the motion of the heart. (Such tracking could be feasible for a robot driven by the processing circuitry.) To alleviate this difficulty, the guidance processor selects a single location within the trajectory of motion found at step 136 and guides the operator to aim at the selected location. Console 28 measures the flow through the stent at this location, at a flow measurement step 142, and thus provides an indication of the extent of any restenosis.

To select the target location at step 140, guidance processor 66 may, for example, find the center of mass of the trajectory found at step 136, and then choose a point that is displaced from the center toward the end of the trajectory that has the greater dwell time, which is the diastolic end. Blood flow through the coronary arteries occurs mainly during diastole, so that the diastolic end of the trajectory will give the strongest Doppler signal. Furthermore, aiming the ultrasound transducer toward the end of the trajectory with the greater dwell permits the ultrasonic beam to capture the stent for a longer part of each heart cycle and thus improves the signal/noise ratio.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A diagnostic apparatus, comprising:
an antenna, which is configured to direct radio frequency (RF) electromagnetic waves into a living body and to generate signals responsively to the waves that are scattered from within the body; and
processing circuitry, which is configured to process the signals so as to locate a feature in the body responsively to a difference in a dielectric constant of the feature relative to surrounding tissue, wherein a front surface of the antenna comprises a printed circuit board, and a planar element of an antenna element of the antenna comprises a conductive radiator printed on the printed circuit board.

2. The apparatus according to claim 1, wherein the antenna comprises an array of antenna elements, which is brought into contact with an outer surface of the body.

3. The apparatus according to claim 1, further comprising an ultrasound transducer, wherein the processing circuitry is configured to guide the ultrasound transducer to direct an ultrasonic beam toward the feature.

4. The apparatus according to claim 3, wherein the feature located by the processing circuitry comprises a stent, and wherein the ultrasound transducer is configured to generate a Doppler signal responsively to a flow of blood through the stent.

5. The apparatus according to claim 3, further comprising a tracking unit configured to track respective coordinates of the antenna and of the ultrasound transducer, wherein the processing circuitry is configured to guide the ultrasound transducer responsively to the respective coordinates.

6. The apparatus according to claim 5, and comprising position transducers fixed respectively to the ultrasound transducer and to the antenna, wherein the tracking unit is configured to track the respective coordinates responsively to position signals exchanged between the position transducers and the tracking system.

7. The apparatus according to claim 1, wherein the processing circuitry is further configured to process the signals so as to perform one or more of detecting, measuring, imaging, and tracking the feature.

8. The apparatus according to claim 3, and comprising a display, wherein the processing circuitry is configured to guide the ultrasound transducer by driving the display to present to an operator of the ultrasound transducer an indication of a direction in which the ultrasound transducer should be aimed.

9. The apparatus according to claim 1, wherein the feature is located in a coronary artery blood vessel.

10. The apparatus according to claim 9, wherein the processing circuitry is configured to track a cyclical motion of the feature over multiple cycles of a heart in the body.

11. A diagnostic apparatus, comprising:
an antenna, having a front surface configured to be brought into contact with an outer surface of a living body so as to direct radio frequency (RF) electromagnetic waves into the body and to generate signals responsively to the waves that are scattered from within the body;
a dielectric gel, which is adapted to be spread between the outer surface of the body and the front surface of the antenna; and
processing circuitry, which is configured to process the signals so as to locate a feature in the body responsively to a difference in a dielectric constant of the feature relative to surrounding tissue, wherein the front surface of the antenna comprises a printed circuit board, and a planar element of an antenna element of the antenna comprises a conductive radiator printed on the printed circuit board.

12. The apparatus according to claim 11, wherein the body has a first dielectric constant, and the gel has a second dielectric constant that is chosen to at least substantially match the first dielectric constant.

13. The apparatus according to claim 11, wherein the gel has a dielectric constant that is between 30 and 75.

14. The apparatus according to claim 11, wherein the gel is adhesive.

15. The apparatus according to claim 11, wherein the gel is water-based and comprises an additive selected from a group of additives comprising an alcohol, a salt, a sugar, and glycerin.

16. The apparatus according to claim 11, wherein the gel comprises silicone and an additive configured to cause the gel attain a dielectric constant that substantially matches an effective dielectric constant of the outer surface of the body on which the gel is spread.

17. The apparatus according to claim 11, wherein the antenna comprises an array of antenna elements, each comprising a planar element at the front surface of the antenna and a cavity behind the planar element.

18. A diagnostic apparatus, comprising:
an antenna, which has a front surface and is configured to direct radio frequency (RF) electromagnetic waves from the front surface into a living body and to generate signals responsively to the waves that are scattered from within the body, and which comprises an array of antenna elements, each antenna element comprising a planar element at the front surface of the antenna and a cavity behind the planar element; and
processing circuitry, which is configured to process the signals so as to locate a feature in the body responsively to a difference in a dielectric constant of the feature relative to surrounding tissue, wherein the front surface of the antenna comprises a printed circuit board, and wherein the planar element of each antenna element comprises a conductive radiator printed on the printed circuit board.

19. The apparatus according to claim 18, wherein the front surface of the antenna is configured to be brought into contact with an outer surface of the body for transmission of the RF electromagnetic waves into the body.

* * * * *